(12) United States Patent
Weissman et al.

(10) Patent No.: US 6,346,399 B1
(45) Date of Patent: Feb. 12, 2002

(54) METHODS FOR REDUCING THE COMPLEXITY OF DNA SEQUENCE

(75) Inventors: Sherman Weissman, New Haven; Roger Lasken, Guilford; Xinghua Pan, West Haven, all of CT (US)

(73) Assignees: Yale University, New Haven; Molecular Staging, Inc., Guilford, both of CT (US)

( * ) Notice: Subject to any disclaimer, the term of this patent is extended or adjusted under 35 U.S.C. 154(b) by 0 days.

(21) Appl. No.: 09/562,331

(22) Filed: May 1, 2000

Related U.S. Application Data

(62) Division of application No. 09/398,217, filed on Sep. 17, 1999.
(60) Provisional application No. 60/100,999, filed on Sep. 18, 1998.

(51) Int. Cl.$^7$ ............................................... G01N 33/00
(52) U.S. Cl. ........................... 435/94; 435/6; 435/91.1; 536/23.1; 536/24.3; 536/25.32
(58) Field of Search ........................ 435/6, 91.1, 91.2, 435/91.51, 183; 436/94; 536/23.1, 24.3, 24.33, 25.3, 25.32

(56) References Cited

U.S. PATENT DOCUMENTS 5,556,750 A    9/1996   Modrich et al.
5,955,276 A  * 9/1999   Morgante et al. ............... 435/6

OTHER PUBLICATIONS

Nelson, Nature Genetics (1993), vol. 4: 11–18.
Straus et al. "Genomic subtraction for cloning DNA corresponding to deletion mutations" Proc. Natl. Acad. Sci. vol. 87, pp. 1889–1893, Mar. 1990.
McAllister et al. "ERnrichment for Loci Identical–by Descent between pairs of Mouse or Humam genomes by Genomic Mismatch Scanning" Genomics, vol. 47, pp. 7–11, Jan. 1998.
Cheung et al. "Genomics Mismatch Scanning: Applications to linkage and linkage disequilibrium analysis" Am. J. of Human Genetics, vol. 61, No. 4, Suppl. pp. A271, Oct. 1997.
Riley et al. "A novel, rapid method for the isolation of terminal sequences from YAC clones" Nucleic Acid Reseach, vol. 18, No. 10, pp. 2887–2890, 1990.
Prasher & Weissman Proc. Nat. Acad. USA (1996) 93: 659–663.
Geung et al. Nature Genetics (1998), 18: 225–230.
Nelson et al., Genomic mismatch scanning: a new approach to gentic linkage mapping. Nature Genetics 4, 11–18, May 1993.*
Cheung et al., Genomic mismatch scanning identifies human genomic DNA shared identical by descent. Genomics 47, 1–6, 1998.*

* cited by examiner

Primary Examiner—Ethan Whisenant
Assistant Examiner—Frank Lu
(74) Attorney, Agent, or Firm—Banner & Witcoff

(57) ABSTRACT

Genomic or cDNA, or fragments and mixtures thereof, can be screened by generation of subsets and then subjecting the subsets to mismatch scanning procedures. Alternatively, DNA fragments can be generated by cutting with a restriction endonuclease that generates variable overhangs. For either of the above methods, Y-shaped adapters having a region of non-complementary single-stranded DNA at the end can be used. Heterohybrid DNA, containing one DNA strand derived from each of two different samples, or homohybrids, containing DNA strands from the same sample, can be selected. Adapters attached to the ends of the fragments are designed to allow the selective isolation of homohybrid or heterohybrid DNA.

17 Claims, 2 Drawing Sheets

↓ ligase

↓ add first primer,
↓ denature, reanneal

↓ DNA pol, dNTPs

↓ capture tag
↓ Mbo 1 cDNA Sau3A1 FRAGMENTS WITH Y SHAPED ADAPTERS. AMPLIFICATION WITH DIFFERENT PRIMER PAIRS cDNA CUT WITH Sau3A1 → LIGATE TO A PAIR OF ADAPTERS → PCR AMPLIFICATION WITH DIFFERENT PRIMER PAIRS

PS1, PS1'
PS2, PS2'
NN / NNN

WELL 1: PS1CG + PS2AG; WELL 2: PS1CGT + PS2AGG; WELL 3: PS1CGT + PS2TCG

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:  DNA
      adaptor for cutting by Sau3A1 restriction endonuclease.

<400> SEQUENCE: 1
cgtccggcgc agcgacggtc ag                                                  22

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: DNA
      adaptor for cutting by Sau3A1 restriction endonuclease.

<400> SEQUENCE: 2
gatcctgacc gtccatctct gtcgcagcg                                           29

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:  PCR primer
      corresponding DNA adaptor shown in SEQ ID NO:1.

<400> SEQUENCE: 3
cgtccggcgc agcgacggtc aggatccg                                            28

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: PCR primer
      corresponding to DNA adaptor shown in SEQ ID NO:2.

<400> SEQUENCE: 4
cgctgcgaca gagatggacg gtcaggatca g                                        31

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:  PCR primer
      corresponding to DNA adaptor shown in SEQ ID NO:1.

<400> SEQUENCE: 5
cgtccggcgc agcgacggtc aggatccgt                                           29

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: PCR primer
      corresponding to DNA adaptor shown in SEQ ID NO:2.

<400> SEQUENCE: 6

-continued cgctgcgaca gagatggacg gtcaggatca gg                                      32

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR primer
      corresponding to DNA adaptor shown in SEQ ID NO:1.

<400> SEQUENCE: 7
cgtccggcgc agcgacggtc aggatccgt                                          29

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: PCR primer
      corresponding to DNA adaptor shown in SEQ ID NO:2.

<400> SEQUENCE: 8
cgctgcgaca gagatggacg gtcaggatct cg                                      32

METHODS FOR REDUCING THE COMPLEXITY OF DNA SEQUENCE

This application is a divisional of U.S. Ser. No. 09/398,217, filed Sep. 17, 1999, still pending.

This application claims the benefit of application Ser. No. 60/100,999 filed Sep. 18, 1998

Technical Field of the Invention

This invention relates to methods for reducing the complexity of DNA mixtures, subsequent analysis of genetic variations, and isolation of probes or clones of regions of interest.

Background of the Invention

In 1993 Nelson and associates described a "genomic mismatch scanning" (GMS) method to directly identify identical-by-descent (IBD) sequences in yeast (Nelson, S. F., et al, *Nature Genetics*, 1993, 4:11–18; this and other papers, books and patents cited herein are expressly incorporated in their entireties by reference). The method allows DNA fragments from IBD regions between two relatives to be isolated based on their ability to form mismatch-free hybrid molecules. The method consists of digesting DNA fragments from two sources with a restriction endonuclease that produces protruding 3'-ends. The protruding 3'-ends provide some protection from exonuclease III (Exo III), which is used in later steps. The two sources are distinguished by methylating the DNA from only one source. Molecules from both sources are denatured and reannealed, resulting in the formation of four types of duplex molecules: homohybrids formed from strands derived from the same source and heterohybrids consisting of DNA strands from different sources. Heterohybrids can either be mismatch-free or contain base-pair mismatches, depending on the extent of identity of homologous regions.

Homohybrids are distinguished from heterohybrids by use of restriction endonucleases that cleave fully methylated or unmethylated GATC sites. Homohybrids are cleaved into smaller duplex molecules. Heterohybrids containing a mismatch are distinguished from mismatch-free molecules by use of the *E. coli* methyl-directed mismatch repair system. The combination of three proteins of the methyl-directed mismatch repair system MutS, MutL, and MutH (herein collectively called MutSLH) along with ATP introduce a single-strand nick on the unmethylated strand at GATC sites in duplexes that contain a mismatch (Welsh, et al., *J Biol. Chem.*, 1987, 262:15624). Heterohybrids that do not contain a mismatch are not nicked. All molecules are then subjected to digestion by Exo III, which can initiate digestion at a nick, a blunt end, or a recessed 3'-end, to produce single-stranded gaps. Only mismatch-free heterohybrids are not subject to attack by Exo III; all other molecules have single-stranded gaps introduced by the enzyme. Molecules with single-stranded regions are removed by absorption to benzoylated napthoylated DEAE cellulose. The remaining molecules consist of mismatch-free heterohybrids which may represent regions of IBD.

Nelson, et al., used *S. cerevisiae* hybrids as a model system and showed that sequences shared by two independently generated hybrids from the same parent strains could be identified in many instances. Experiments of this kind are much easier to do in yeast than in humans. The yeast genome is 250 times simpler than the human genome, it contains far fewer repetitive sequences, and genomic sequences of two yeast strains differ more than genomes of unrelated humans. It has thus far not been possible to do comparable experiments with human genomic DNA. In order to do so one needs to use methods to reproducibly generate simplified but highly polymorphic representations of the human genome. Pooling techniques based on mathematical principles are also essential to identify IBD sequences as well as other sequences showing allele frequency differences (AFD) (Shaw, S. H., et al., *Genome Research*, Cold Spring Harbor Laboratory Press, 1998, 8:111–123).

The human genome is enormously long, at $3 \times 10^9$ base pairs, and it is far too complex for efficient reannealing of homologous DNA strands after denaturation. The rate of annealing of a mixture of nucleic acid fragments in liquid phase is inversely proportional to the square of their complexity. Efforts have therefore been made to generate simplified representations of the genome for genetic methods based on cross hybridization of homologous sequences from different genomes. The exact degree of simplification of human genomic DNA needed to achieve efficient annealing depends on the conditions of hybridization including total DNA concentration, hybridization buffer, and temperature. In general a 10–100 fold simplification is needed for efficient annealing to occur at high DNA concentrations in high salt aqueous solutions (Lisitsyn, N. A., et al., *Science*, 1993, 259:946–951).

In some embodiments of the invention, DNA sequences of interest are replicated in rolling circle amplification reactions (RCA). RCA is an isothermal amplification reaction in which a DNA polymerase extends a primer on a circular template (Kornberg, A. and Baker, T. A., *DNA Replication*, W. H. Freeman, New York, 1991). The product consists of tandemly linked copies of the complementary sequence of the template. RCA can be used as a DNA amplification method (Fire, A. and Si-Qun Xu, *Proc. Natl. Acad. Sci. USA*, 1991, 92:4641–4645; Lui, D., et al. *J Am. Chem. Soc.*, 1995, 118:1587–1594; Lizardi, P. M., et al., *Nature Genetics*, 1998, 19:225–232). RCA can also be used in a detection method using a probe called a "padlock probe" (Nilsson, M., et al., *Nature Genetics*, 1997, 16: 252–255).

It would be useful to have superior ways of analyzing human DNA and other complex DNA samples.

SUMMARY OF THE INVENTION

A general method for screening genomic or cDNA, or fragments and mixtures thereof, involves sample simplification by the generation of subsets and then subjecting the subsets to mismatch scanning procedures. Any given DNA sequence will be represented in one and only one subset, minimizing the number of subsets required to detect a sequence of interest and guaranteeing that all possible sequences can potentially be covered by analyzing all possible subsets. The complexity of DNA sequences is reduced by attaching adapters to the ends of DNA fragments that allow the specific subsets of DNA to be selected and amplified. In some procedures, subsets are generated by replicating DNA in a polymerase chain reaction (PCR) or single primer extension reactions using primers that are complementary to sequences in the adapter and which, at the 3'-end, are complementary to a subset of sequences in the genomic or cDNA.

In another version of this method, DNA fragments are generated by cutting with a restriction endonuclease, such as Bsl1, that generates variable overhangs for which some of the nucleotides can have any of 2 to 4 of the bases A, C, G, or T. In this case, subsets are generated by ligating adapters to the fragment ends that have a specific sequence in the overhang and a primer binding site unique for each adapter. For either of the above methods, Y-shaped adapters can be used having a region of non-complementary single-stranded DNA at the end. Therefore, following ligation, the DNA fragment-plus-adapter construct has the non-complementary region at its ends. Use of Y-shaped adapters make it possible to generate non-overlapping subsets such that a given DNA fragment will only be represented in one of the possible subsets.

Procedures are given for isolating selected subsets from other, contaminating DNAs by using primers that have attached chemical moieties that can be captured on beads, columns, and the like. In some cases, the DNA is then released by cutting specifically designed sequences in the primers with restriction endonucleases. Fragment DNA is protected from these restriction endonucleases by methylation. The DNA subsets obtained are sufficiently reduced in complexity to allow improved analysis of sequence polymorphism by mismatch scanning procedures. Procedures are given for selecting DNA fragments representing regions of low polymorphism or for generating fragments depleted for regions of low polymorphism.

In some embodiments, the DNA fragments are replicated in a rolling circle amplification procedure (RCA; see reviews by Hingorani, M. M., and O'Donnell, M., *Current Biology*, 1998, 8:R83-86 and by Kelman, Z., et al., *Structure*, 1998, 6:121–5). The DNA polymerase III holoenzyme (hereafter sometimes denoted DNA pol III) is used in most of these methods to increase the rate and processivity of primer extension. DNA pol III also improves the ability to replicate through a DNA region of high GC content or other obstructions that tend to block DNA polymerases.

A method is also given for selecting heterohybrid DNA that contains one DNA strand derived from each of two different samples or homohybrids in which the DNA strands from different samples have not been recombined. Each DNA sample may consist of some concentration of a unique DNA fragment, or a mixture of fragments, and each sample may be derived from a single individual or more than one individual. The different DNA samples are mixed together, denatured, and then reannealed. Some of the DNA strands will reanneal back together with another strand from the same DNA sample forming a homohybrid. Other DNA strands will reanneal with a DNA strand from a different sample forming a heterohybrid. Adapters attached to the ends of the fragments are designed to allow the selective isolation of homohybrid or heterohybrid DNA. In one method, restriction endonuclease recognition sites are present in the adapters such that homohybrid or heterohybrid DNA can be selectively eliminated depending on the ability of the restriction endonuclease to cut the DNA.

DETAILED DESCRIPTION OF THE INVENTION

This invention provides for the screening of complex DNA preparations, including complex DNA comprised of genomic segments or cDNAs, and the isolation of genes without requiring prior knowledge of their biochemical function or map position. Methods of the invention divide DNA into subsets and then manipulate the subsets using a mismatch repair system and capture techniques to obtain specific DNA sequences, including genomic subsets of long genomic DNA generated by selective amplification of sequences exhibiting low polymorphism.

As used herein, "polymorphism" refers to genetic sequence variation between different individuals of a species. A "homoduplex" is double-stranded DNA where both strands derive from the same genome or pools of genome samples, and a "heteroduplex" is double-stranded DNA where each strand originated from different genomes or different pools of genomes. By "perfectly matched" is meant double-stranded DNA where each base residue is correctly paired with a base on the opposite strand, i.e., A to T and C to G. By "mismatched" is meant double-stranded DNA where at least one base residue on either strand is either not paired with any residue, or paired with an incorrect base, i.e., A not paired with T, C not paired with G.

In a typical practice of a method of the invention, at least one DNA sample is methylated, usually at the GATC sites with bacterial DAM methylase, and the sample is then cut with an enzyme that makes infrequent cuts such as PvuI (Nelson, S. F., et al., cited above). Any type of DNA sample may be subjected to methods of the invention, including genomic DNA, genomic fragments, cDNA, cDNA fragments, and mixtures of any of these. It is an advantage of the invention that it can be used to identify identical-by-descent sequences of low polymorphism in complex human or other genomic DNA samples. It can also be used to identify sequences of high polymorphism.

Adapters are then ligated to the fragments to obtain fragment-plus-adapter constructs. Linear or Y-shaped adapters may be employed. Y-shaped adapters are used in many preferred embodiments, but, in some cases, where Y-shaped adapters are illustrated, the methods can also be adapted to conventional linear adapters. Y-shaped adapters have been described (see Prashar, Y., and Weissman, S., *Proc. Natl.*

Figure 1A:
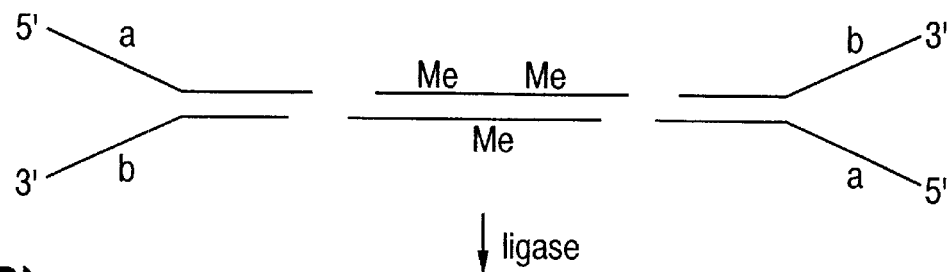
In FIG. 1A and FIG. 1B), Y-shaped adapters having non-complementary sequences on one end and appropriate overhangs for ligation on the other end are ligated to DNA fragments.
Figure 1B:
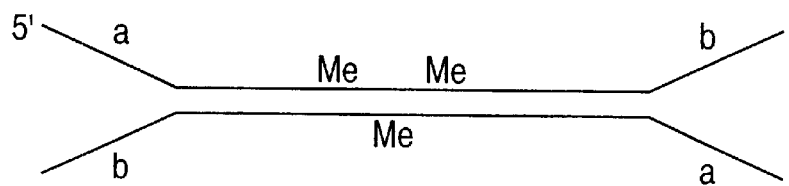

Acad. Sci. USA, 1996, 93:659–663). A Y-shaped adapter typically has an overhang on its 3'-end for ligation, and on the 5'-end, a stretch of noncomplementary sequence on the opposite strands, giving rise to its Y-shape (see FIG. 1A and B). It is an advantage of the invention that, in preferred embodiments, the Y-shaped adapters allow for the synthesis of non-overlapping subsets of DNA. In typical embodiments, if the invention is carried out with conventional, linear primers, then the PCR-generated subsets will be partially overlapping, that is, some DNA sequences will be represented in more than one subset.

The fragment-plus adapter constructs are subjected to a PCR or to a single primer extension reaction in the presence of a primer complementary to at least a portion of the adapter at the 3'-end of the fragment-plus-adapter constructs and extending across the adapter ligation, and having at least one nucleotide overlap into the DNA fragment sequence. As used herein, a "polymerase chain reaction" includes conventional PCR, as well as modifications employing betaine, proof-editing polymerases, DMSO, and the like, and combinations thereof Likewise, "rolling circle amplification" includes variants described by Hingorani and O'Donnell, cited above, and specifically encompasses modifications using a reconstituted bacterial polymerase III system including holoenzyme, helicase, clamp proteins, and clamp loading proteins (Bloom, L. B., et al., *J. Biol. Chem.*, 1997, 272:27919–27930).

Figure 1C:
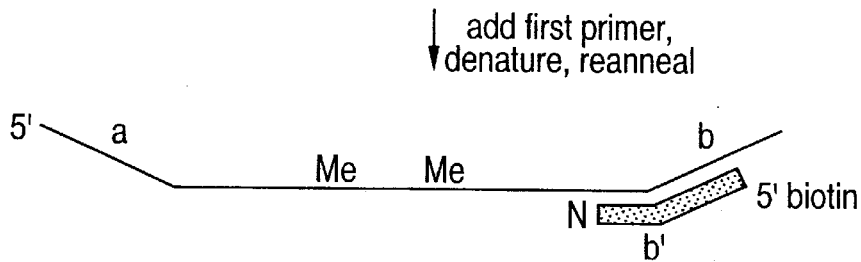
In FIG. 1C, a primer is annealed to the denatured fragment-plus-adapter construct for use in single primer extension, PCR or other DNA polymerase reaction. The 5'-end of the primer consists of a sequence complementary to the adapter region (b) and, at the 3'-end, the primer has one or more nucleotides (N) which must properly anneal to the fragment sequence in order for priming to occur. Therefore, only a subset of fragment sequences that are complementary to the nucleotide(s) N of the primer will be replicated. A capture moiety, in this case biotin, can be present to allow isolation of reaction products.
Figure 1D:
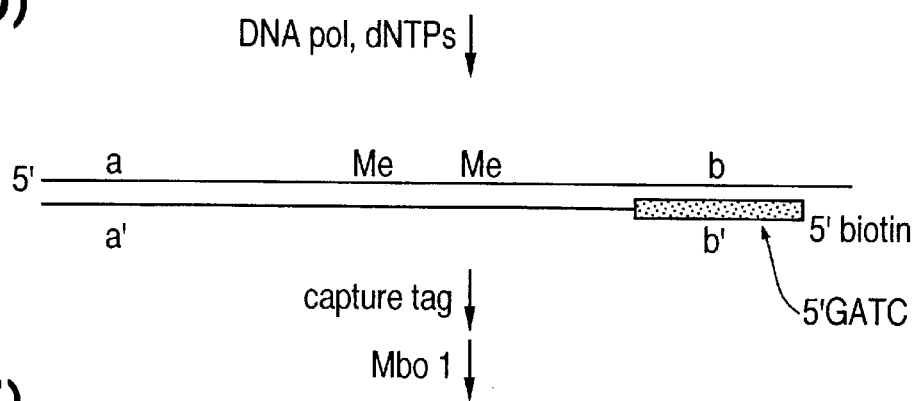
In FIG. 1D, extension of the primer by DNA polymerase generates a product, the 3'-end of which is complementary to the adapter region (a). Therefore, this DNA product can itself be replicated by use of a primer complementary to the sequence (a) in a primer extension, PCR, or other DNA polymerase reaction. Because of the Y-shaped adapters, the products of such replication reactions will be in non-overlapping subsets defined by the nucleotide(s) N of the primer. The presence of a restriction endonuclease recognition site in the adapter, in this case GATC (FIG. 1D), allows for the release of any DNA product following capture by the moiety as shown in FIG. 1E.
Figure 1E:
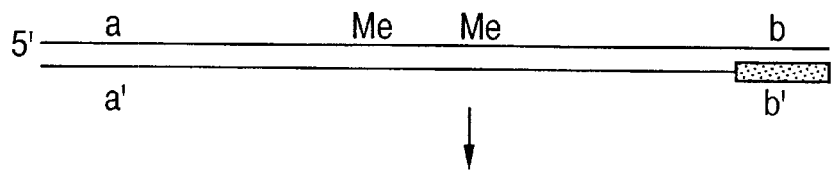
FIG. 1 is a diagram illustrating the addition of Y-shaped adapters to DNA fragments and generation of subsets reducing the complexity of the sequences.

In some cases, a tag at the 5'-end, and a restriction endonuclease recognition site at least about 6 nucleotides from the tag, are present to allow capture of a DNA product and subsequent release by cutting with the restriction endonuclease. In some embodiments, the annealed primer extends across the adapter ligation site one nucleotide into the DNA fragment sequence; in others, they extend two; and in others, more than two. The number of nucleotides, and the identity of the nucleotides that the primer extends across the adapter ligation site, determines the members of the subset to be amplified. The tag in many embodiments is biotin, illustrated in FIG. 1C.

In an alternative method for generating subsets, DNA samples are cut with a restriction endonuclease, such as Bsl1, that generates variable overhangs. That is, some of the bases in the recognition site can be of any-two or more of the four possible bases G, A, T, or C. Adapters having overhangs complementary for this restriction endonuclease recognition site are ligated onto the fragments. Adapter overhangs having a unique sequence for the variable sites will only ligate to a subset of fragments that are complementary at those positions. Therefore, a subset of fragments will be replicated by a primer complementary to the adapter. By employing Y-shaped adapters, the subsets will be non-overlapping. Another advantage of this method is that it is a simple process to ligate adapters of one sequence at one end of the fragment and adapters of a second sequence at the other end of the fragment. If the adapters differ from each other in the primer annealing sequence of their non-complementary (Y-shaped) regions, then it is possible to amplify only one strand of the duplex adapter-fragment complex with the appropriate primer set in a PCR or other DNA polymerase reaction.

In a typical practice of a method of the invention, a subset of fragments are generated from one sample of a DNA or a mixture of DNAs, and these are methylated. The same subset is obtained from a second sample of DNA or mixture of DNAs, and these are not methylated. Mixing, denaturing and reannealing the methylated and unmethylated samples together generates hemimethylated heterohybrids, and, where a large number of DNA samples have been pooled together, most of the reannealed duplex DNA will be heterohybrids. The reannealing thus primarily results in perfectly matched heterohybrids or mismatched heterohybrids, depending upon the degree of polymorphism of the samples. In some cases, the mismatched heterohybrids are then selected by binding of MutS to the mismatch or subjected to MutSLH, which nicks any that contain the mismatched base pairs expected for regions of high polymorphism (see U.S. Pat. No. 5,556,750 to Modrich, et al., Cheung, V. G., et al., *Nature Genetics*, 1998, 18:225–230, and the references cited therein).

In the case where samples are treated with MutSLH, the nick that is generated in mismatched DNA is utilized to identify, isolate, amplify, or clone these fragments using a variety of methods that take advantage of the nick. In one case, a capture agent such as a biotin-tagged nucleotide is added onto the nick by terminal transferase or some other DNA polymerase and the nicked fragment is thereby isolated. Alternatively, the nicked strand can be removed by treatment with an exonuclease according to a published method (Nelson, S. F., et al., cited above). The surviving strand is then selected by DNA amplification or other methods. In another use of MutSLH nicked DNA, the 3'-OH of the nick serves as a primer for a DNA polymerase. Extension of the 3'-OH requires that the DNA polymerase utilize a duplex DNA template by a nick translation or strand displacement reaction. The newly synthesized DNA can be detected by the incorporation of a radioactively or fluorescently labelled nucleotide, or captured by the incorporation of a nucleotide appropriately tagged with a capture agent such as biotin. Also, extension of the nick where the Y-shaped adapter-fragment constructs of this invention are employed results in a DNA product which can be specifically replicated with unique primer sets in a PCR reaction or with a unique "splint oligonucleotide" in a rolling circle amplification. Referred to above, RCA is an isothermal amplification reaction in which a DNA polymerase extends a primer on a circular template (see Kornberg and Baker and other references cited above). The product consists of tandemly linked copies of the complementary sequence of the template.

In the case of RCA, the "splint oligonucleotide" is frequently a single-stranded sequence complementary to the ends of the DNA that results from extension of the nick such that denaturation of the DNA and annealing of the splint to the extended strand circularizes it. If the DNA is circularized such that its two ends are brought together at a nick, then the ends can be ligated together by DNA ligase forming a covalently closed circle. This DNA can then be amplified in an RCA. Another aspect of this invention is that DNA polymerase III holoenzyme derived from *E. coli* or other bacteria, including gram-positive and gram-negative bacteria, or related DNA polymerases from eukaryotes that have clamp (PCNA) and clamp loader (RFC) components (Kornberg and Baker, cited above) can be employed as the DNA polymerase in RCA. Use of DNA pol III is advantageous in many embodiments because pol III has a greater rate and processivity than other DNA polymerases and provides superior yield and ability to replicate long templates and templates having obstructions to DNA replication such as high GC content, or unfavorable secondary structure or sequence context. The *E. coli* dnaB and dnaC proteins or other helicases and the single-stranded DNA binding protein (SSB) can also be used to facilitate the reaction (Kornberg and Baker, cited above).

In another use of the nick generated in mismatched DNA by MutSLH, the mismatched DNA is discarded and the perfectly matched DNA can thereby be selectively amplified. For example, PCR primers, or a splint oligonucleotide in the case of RCA, can be used to amplify those DNAs not nicked by MutSLH whereas nicked DNA cannot provide an intact DNA template.

The methods employed in this invention depend on the isolation of heterohybrid DNA in which the two strands are derived from two different DNA samples. This can be accomplished by published methods (Nelson, et al., cited above). Improved procedures that do not require methylation of fragment DNA are included in this invention. Sequences in the adapters are designed to allow selective cutting of homohybrid or heterohybrid DNA with restriction endonucleases. In some methods, the adapters contain two adjacent restriction enzyme recognition sites with specific methylation patterns such that heterohybrid and homohybrid DNAs can be distinguished by the ability of the methyl groups to block cutting by the restriction endonuclease. In other methods, partial restriction endonuclease recognition sequences are present in which the adapter contains mismatched bases. In this case heterohybrid and homohybrid DNAs can be distinguished by the elimination of the mismatches which allows restriction endonuclease to cut these sites.

EXAMPLES

Example 1. Procedure for creating cDNA or Genomic DNA Subsets

This example illustrates the use of PCR to amplify a subset of cDNA The method can be used also for total genomic DNA or other mixtures of DNAs. The Y shaped adapters are designed two create "butterfly" ends on the construct (see FIG. 2). The Y type adaptors enable only one strand but not the other strand of the fragment to be amplified. Also, both strands can be amplified separately. This is useful when the fragment contains a mismatched base pair and it is desirable to amplify the strands separately. The Y shaped adapters also enable the amplified duplex to be sequenced. The PCR primers are designed so that their 5' end is complementary to adapter sequence, but 1–3 nucleotides at their 3' end (designated by "N" in FIG. 2) must base pair with the target DNA insert. The target DNA sequences that will be amplified are determined by the identity of the 3' terminal nucleotides of the PCR primers. Therefore, only a subset of sequences will be amplified and the complexity of the sample will be reduced.

In this example, cDNA was cut with a 4 nucleotide-recognizing restriction enzyme, Sau3AI. The restriction enzyme was inactivated after digestion was completed by treating it at 65C for 30 minutes. The digested DNA was then purified by phenol chloroform extraction. Y shaped adaptors were formed by annealing as follows: 1.3 nmol XS1, 1.3 nmol XS2, 5 mM Tris-HCl pH7.5 and 100 mM NaCl in 100 microliters volume at 94C×10 min, cool down to 37C×2 hrs, then 32C×2 hrs, 30C×2 Hrs, 28×2 Hrs, 25×2 Hrs and on ice. The fragments were then ligated to Y shaped adaptors as follows: cut cDNA 0.1 micrograms, adaptor pair 0.2 micrograms /13 pmol, ligase 8u and 1X ligase buffer in 5 microliters at 16C overnight. A subset of the sequences was then amplified with a pair of PCR primers (see primer sequences below) in the following mixture: 2 microliters of 200-fold diluted ligated product from above, 2ul of 2 micromolar each primer, 0.75 units AmpliTaq Gold DNA Polymerase (Perkin Elmer), 2 mM each dNTP and 1X DNA polymerase buffer supplied by the manufacturer. The PCR was done in a Perkin Elmer Cetus Gene Amp PCR System 9600 with the program:

95C, 4min
five cycles
94C, 30 sec
55C, 30 sec
72C, 30 sec
25 cycles
94C, 30 sec
65C, 30 sec
72C, 30 sec
72C, 5 min.

Figure 2:
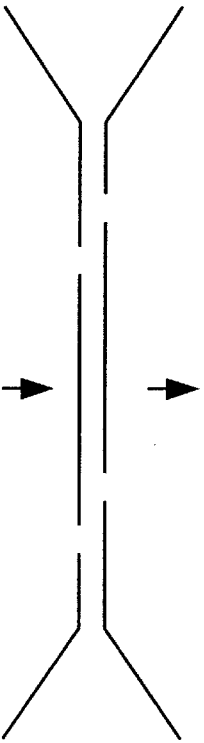
FIG. 2A shows cDNA Sau3A1 fragments with Y shaped adapters and amplification with different primer pairs.
FIG. 2B shows the results of amplification with three different primer pairs.
Figure 2:
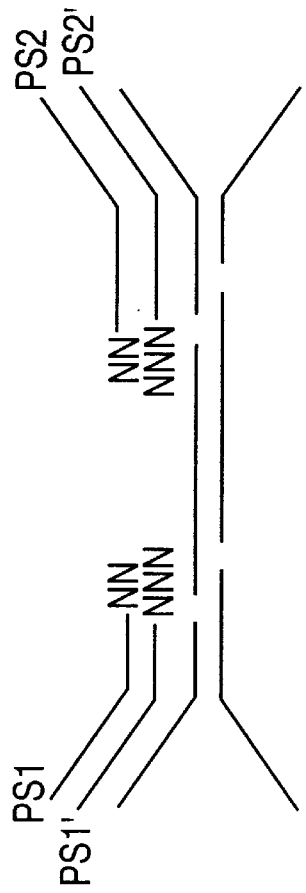
Figure 2:
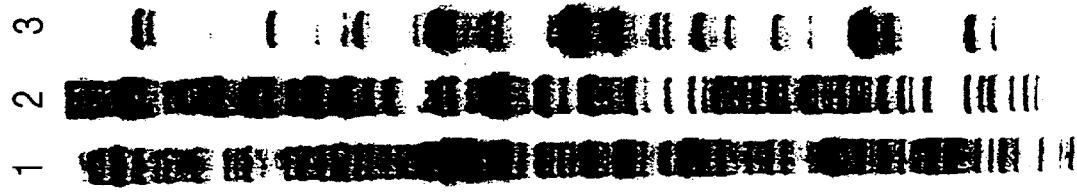

As indicated in FIG. 2, three different primer sets were used. Well number 1 contained a primer sequence which has C and G as the two 3' terminal nucleotides (designated PS1CG), and PS2AG which has A and G as the terminal nucleotides. Wells 2 and 3 of FIG. 2 contained primer sets with different terminal nucleotides as indicated. As expected, the three PCR reactions produced different band patterns determined by which primer set was used.

Adaptor for Sau3AI cutting

XS1 (22 nt )
CGTCCGGCGCCAGCGACGGTCAG—SEQ ID No: 1

XS2 (29 nt)
GATCCTGACCGTCCATCTCTGTCGCAGCG—SEQ ID No: 2

PCR Primers (corresponding to above Sau3AI adaptors):
Set1:
PS1CG (28 nt)
CGTCCGGCGCAGCGACGGTCAGGATCCG—SEQ ID No: 3

PS2AG (31 nt)
CGCTGCGACAGAGATGGACGGTCAGGATCAG—SEQ ID No: 5

Set2:
PS1CGT (29 nt)
CGTCCGGCGCAGCGACGGTCAGGATCCGT—SEQ ID No: 5

PS2AGG0 (32 nt)
CGCTGCGACAGAGATGGACGGTCAGGATCAGG—SEQ ID No: 6

Set3:
PS1CGT (29 nt)
CGTCCGGCGCAGCGACGGTCAGGATCCGT—SEQ ID No: 7

PS2TCG (32 nt)
CGCTGCGACAGAGATGGACGGTCAGGATCTCG—SEQ ID No: 8

The above description is for the purpose of teaching the person of ordinary skill in the art how to practice the present invention, and it is not intended to detail all those obvious modifications and variations of it which will become apparent to the skilled worker upon reading the description. For example, there are numerous variations of steps in the overall procedures, and for preparing the probes. Variations in primers having larger overlap with DNA fragments and various amplification techniques, for example, have already been mentioned. Following selective isolation of duplex DNA, it could be transcribed with T7 or other appropriate RNA polymerase, and the RNA used as a direct probe, or reconverted into double-stranded DNA in some embodiments. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers, books and patents cited herein are expressly incorporated in their entireties by reference.

What is claimed is:

1. A method for isolating DNA subsets from a first sample and a second sample for use in genomic mismatch analysis, comprising:
  (a) subjecting first portions of said first and second samples separately to a first oligonucleotide consisting of at least two copies of any dinucleotide, trinucleotide, or tetranucleotide repeat attached to a support to obtain first and second sample fractions that bind to the first oligonucleotide;
  (b) subjecting second portions of said first and second samples separately to a second oligonucleotide consisting of at least two adjacent copies of any dinucleotide, trinucleotide or tetranucleotide repeat different than that employed in step (a) attached to a support to obtain first and second sample fractions that bind to the second oligonucleotide;
  (c) mixing the first sample fraction obtained in step (a) with the second sample fraction obtained in step (b), and mixing the second sample fraction obtained in step (a) with the first sample fraction obtained in step (b);
  (d) denaturing and reannealing each mixture to form heterohybrids, wherein the heterohybrids comprise the DNA subsets to be used in genomic mismatch analysis.

2. The method according to claim 1 further comprising the step of subjecting the DNA subsets to genomic mismatch analysis.

3. A method according to claim 2 wherein the first oligonucleotide consists of at least two CA dinucleotide repeats, and the second oligonucleotide consists of at least two GT dinucleotide repeats.

4. A method according to claim 1 comprising the further step of subjecting the heterohybrids to allele frequency differences analysis.

5. A method according to any of claims 2, 3, or 4 comprising the further step of capturing mismatched DNA subsets by incubating the subsets with biotinylated MutS attached to a support bearing avidin or strepavidin.

6. A method according to any of claims 2, 3, or 4 wherein the first and second samples comprise genomic DNA, genomic DNA fragments, or mixtures thereof.

7. A method according to claim 6 wherein the DNA subsets are used to identify genomic IBD sequences.

8. A method according to any of claims 2, 3, or 4 wherein the first and second samples comprise cDNA.

9. A method according to claim 8 wherein the samples are analyzed for differences by separation of the recovered cDNA fragments using techniques selected from the group consisting of sequencing gels, capillaries, mass spectroscopy, labelling with radioisotopes, labelling with antigenic epitopes, labelling with fluorescent dyes, mixing and hybridizing to arrays of genomic DNA clones and combinations of any of these procedures.

10. A method according to claim 8 wherein the samples are analyzed for differences by separation of the recovered cDNA fragments using techniques selected from the group consisting of sequencing gels, capillaries, mass spectroscopy, and combinations of any of these separation techniques.

11. A method according to claim 8 wherein the recovered cDNA fragments are labelled with radioisotopes, antigenic epitopes or fluorescent dyes.

12. A method according to claim 8 wherein the cDNA samples are used to detect homozygosity for mutations in affected subjects, and heterozygosity in carriers.

13. A method according to claim 12 wherein cDNA samples are prepared from homozygous-affected subjects in a family and from one or both parents.

14. A method according to claim 8 wherein the cDNA samples are used to detect new mutations in a subject with de novo dominant mutation, where the parents of the subject do not show the disorder, by analysis of cDNA displays prepared from the subject cDNA, from each subject parent's cDNA, from heterohybrids between subject and parent cDNA, and from heterohybrids prepared between the cDNA of the two parents.

15. A method according to claim 8 wherein the cDNA samples are used to detect mutations in cDNA in cancers that are not present in cDNA of normal tissue from the same subject.

16. A method according to claim 8 which analyzes differences in the relative amounts of heterozygosity in cDNA fragments from control subjects, and from subjects with a genetic disorder of unknown pattern of inheritance or a polygenic disorder.

17. A method according to claim 14 wherein mRNA from a group of control subjects and from a group of subjects with the disorder are prepared, cDNA generated from both RNA groups are prepared, and cDNA displays are analyzed with subject pools, control pools, and pools from heterohybrids between subjects and controls.

* * * * *